United States Patent
Kim et al.

(10) Patent No.: US 7,829,868 B2
(45) Date of Patent: Nov. 9, 2010

(54) METHODS FOR DETECTING FLUORESCENT SIGNALS IN A BIOLOGICAL SAMPLE

(75) Inventors: Young Min Kim, Wallingford, CT (US); Yanning Zhu, Hamden, CT (US); Yash Agarwal, New Haven, CT (US); Xiuzhong Wang, Hamden, CT (US); Aaron Armstrong, Norwalk, CT (US); Robert Borgerding, New Haven, CT (US); Andrew MacGinitie, Roxbury, CT (US); Antti Seppo, New York, NY (US); Ilia Ichetovkin, Hamden, CT (US); Michael Kilpatrick, West Hartford, CT (US); Petros Tsipouras, Madison, CT (US); Triantafyllos Tafas, Rocky Hill, CT (US)

(73) Assignee: Ikonisys, Inc., New Haven, CT (US)

( * ) Notice: Subject to any disclaimer, the term of this patent is extended or adjusted under 35 U.S.C. 154(b) by 375 days.

(21) Appl. No.: 11/833,849

(22) Filed: Aug. 3, 2007

(65) Prior Publication Data
US 2009/0250629 A1 Oct. 8, 2009

Related U.S. Application Data

(60) Provisional application No. 60/821,557, filed on Aug. 4, 2006.

(51) Int. Cl.
*G01N 21/64* (2006.01)
(52) U.S. Cl. .................................................. 250/459.1

(58) Field of Classification Search ............... 250/459.1
See application file for complete search history.

(56) References Cited

U.S. PATENT DOCUMENTS

2003/0120633 A1* 6/2003 Torre-Bueno .................. 707/1
2007/0279735 A1* 12/2007 Sieckmann ................. 359/396

FOREIGN PATENT DOCUMENTS

WO   WO 2005121865 A1 * 12/2005

OTHER PUBLICATIONS

S. Becker, G. Becker-Pergola, T. Fehm, R. Emig, D. Wallweiner, and E-F. Solomayer, "Image Analysis Systems for the Detection of Disseminated Breast Cancer Cells on Bone-Marrow Cytospins," Journal of Clinical Laboratory Analysis, vol. 19, Issue 3, pp. 115-119, published online May 17, 2005, <doi:10.1002/jcla.20064>.*
Taylor et al., "The New Vision of Light Microscopy," American Scientist 80:322-335 (Jul.-Aug. 1992).
Abbot Laboratories d/b/a Urovysion. Urovysion Bladder Cancer Test Kit. © 2007. http://www.urovysion.com/description_284.aspx.
Aneuvysion. About Aneuvysion Home Page. Mar. 31, 2006. http://www.aneuvysion.com/AboutAneuVysion_6.asp.
Abbott Molecular. Assay Procedure. © 2006. http://www.abbottmolecular.com/AssayProcedure_36786.aspx.

* cited by examiner

*Primary Examiner*—Constantine Hannaher
(74) *Attorney, Agent, or Firm*—Kelley Drye & Warre LLP

(57) ABSTRACT

A method for automated microscopic analysis wherein the test protocol is obtained from interrogatable data affixed to each microscope slide. The method further comprises the algorithms that implement the test protocol.

24 Claims, 13 Drawing Sheets

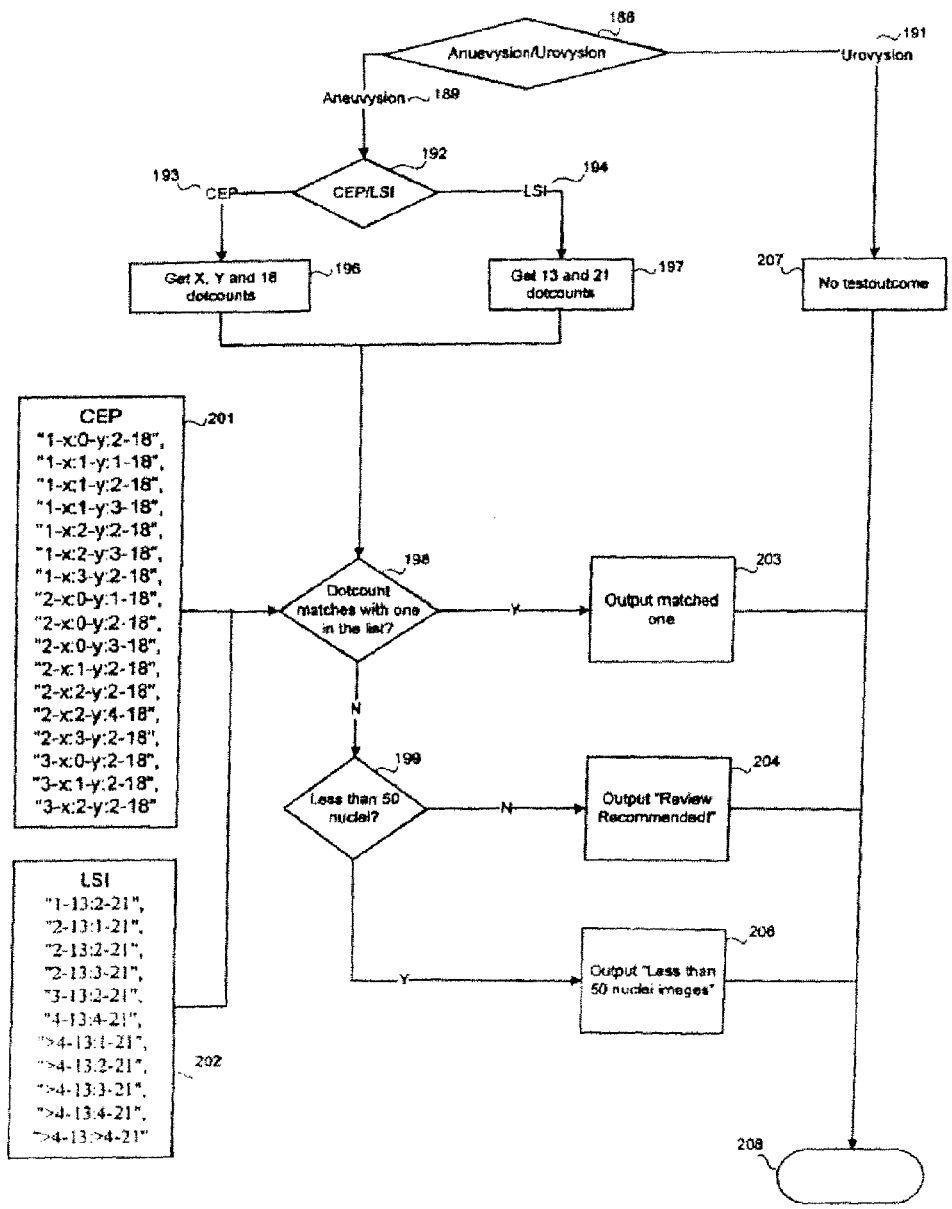

METHODS FOR DETECTING FLUORESCENT SIGNALS IN A BIOLOGICAL SAMPLE

CROSS-REFERENCE TO RELATED APPLICATIONS

This application claims the benefit of priority of U.S. Provisional Application No. 60/821,557, filed Aug. 4, 2006, which is incorporated herein by reference in its entirety.

BACKGROUND OF THE INVENTION

All references cited in this specification, and their references, are incorporated by reference herein where appropriate for teachings of additional or alternative details, features, and/or technical background. Incorporation by reference to non-patent publications is only for nonessential material.

FIELD OF THE INVENTION

The present invention generally relates to the automated microscopic detection of biological structures using fluorescent tags directed to such biological structures.

DESCRIPTION OF THE RELATED ART

Conventional optical microscopy generally employs a microscope slide to which a biological sample has been affixed, and a single objective lens that is used to focus on discrete areas of the biological sample in a search for structures of interest, such as cells, nuclei, etc. Dimensions of the image seen through the objective lens depend on the magnification and numerical aperture of the objective lens. The specimen on the microscope slide is manually moved with respect to the objective lens resulting in a plurality of fields of view. Structures of interest seen through the objective in each field of view are analyzed with image details recorded. Images may be stored by means of acquisition by a camera. The multiple field of view are used to characterize the sample as a whole. Of course, such process may be slow for any application that requires a complete view of the specimen.

Numerous factors must be dealt with in microscopy, including resolution, contrast, depth of focus, working distance, magnification, parfocality, and parcentricity. Resolution is the ability to distinguish in an image two points as two points. Resolution is important to determine differentiate features in a sample. Resolution may decrease with magnification, and is typically related to the numerical aperture of the objective. Contrast is also necessary in the evaluation of an image. Contrast is the difference between the brightest point in an image and the darkest point in the image, or the relative intensity of the zero order versus the diffracted orders. Without sufficient contrast an image may appear "flat" at best, or invisible at worst. Contrast is conventionally controlled in a manual microscope by way of a condenser diaphragm. Depth of focus refers to the depth of the image in focus. Depth of focus changes as the numerical aperture of the objective changes, and the working distance of the objective changes (as the working distance of the objective is increased the depth of focus increases). The depth of focus is important in that objects within the specimen that are outside the depth of focus are not detected. Working distance refers to the distance from the front of the objective to the specimen plane. When objectives are changed working distance (particularly when the objective has a different numerical aperture) may change as well as focus. It is generally important to keep the working distance sufficient so as not to have the objective interfered by the specimen proper. Parfocality, that is the specimen staying in focus when the objective is changed, and parcentricity, that is, an object in the center of the field staying in the center of the field no matter which objective is being used, are also generally desirable.

Many methods are known to aid in the microscopic analysis of samples. For example, without limitation, it is known that certain dyes have an affinity for certain cellular structures. Such dyes may therefore be used to aid in analysis by helping to further elucidate such structures.

Fluorescence microscopy of cells and tissues is well known in the art. Treating cells with fluorescent reagents and imaging the cells is well known in the art. Methods have been developed to image fluorescent cells in a microscope and extract information about the spatial distribution and temporal changes occurring in these cells. Some of these methods and their applications are described in an article by Taylor, et al. in American Scientist 80 (1992), p. 322-335. These methods have been designed and optimized for the preparation of a few specimens for high spatial and temporal resolution imaging measurements of distribution, amount and biochemical environment of the fluorescent reporter molecules in the cells. Detection of fluorescent signals may be by way of an epifluorescent microscope which uses emitted fluorescent light to form an image (whereas a conventional reflecting microscope uses scattered illumination light to form an image). The excitation light of a epifluorescence microscope is used to excite a fluorescent tag in the sample causing the fluorescent tag to emit fluorescent light. The advantage of an epifluorescence microscope is that the sample may be prepared such that the fluorescent molecules are preferentially attached to the biological structures of interest thereby allowing identification of such biological structures of interest.

One fluorescent dye used in flouresence microscopy is DAPI or 4',6-diamidino-2-phenylindole [CAS number: [28718-90-3]; SMILES structure: NC(C2=CC1=C(C=C2)C=C(C3=CC=C(C(N)=N)C=C3)N1)=N], a fluorescent stain that binds strongly to DNA. Since DAPI will pass through an intact cell membrane, it may be used to stain live and fixed cells. DAPI is excited with ultraviolet light. When bound to double-stranded DNA its absorption maximum may be about 358 nm and its emission maximum may be about 461 nm. DAPI will also bind to RNA, though it is not as strongly fluorescent. Its emission shifts to about 400 nm when bound to RNA. DAPI's blue emission is convenient for microscopists who wish to use multiple fluorescent stains in a single sample. There is very little fluorescence overlap, for example, between DAPI and green-fluorescent molecules like fluorescein and green fluorescent protein (GFP), or red-fluorescent stains like Texas Red. Other fluorescent dyes are used to detect other biological structures.

Other types of fluorescing materials are used in fluorescence in situ hybridization (FISH). The FISH method uses fluorescent tags to detect chromosomal structure. Such tags may directed to specific chromosomes and specific chromosome regions. Such technique may be used for identifying chromosomal abnormalities and gene mapping. For example, a FISH probe to chromosome 21 permits one to identify cells with trisomy 21, i.e., cells with an extra chromosome 21, the cause of Down syndrome. FISH kits comprising multicolor DNA probes are commercially available. For example, AneuVysion® Multicolor DNA Probe Kit sold by the Vysis division of Abbott Laboratories, is designed for in vitro diagnostic testing for abnormalities of chromosomes 13, 18, 21, X and Y in amniotic fluid samples via fluorescence in situ hybridization (FISH) in metaphase cells and interphase nuclei. The AneuVysion® Assay (CEP 18, X, Y-alpha satellite, LSI 13 and 21) Multi-color Probe Panel uses CEP 18/X/Y probe to detect alpha satellite sequences in the centromere regions of chromosomes 18, X and Y and LSI 13/21 probe to detect the 13q14 region and the 21q22.13 to 21q22.2 region. The AneuVysion kit is useful for identifying and enumerating chromosomes 13, 18, 21, X and Y via fluorescence in situ hybridization in metaphase cells and interphase nuclei obtained from amniotic fluid in subjects with presumed high risk pregnancies. The combination of colors emitted by the tags is used to determine whether there is a normal chromosome numbers or trisomy.

In a similar vein, the UroVysion® kit by the Vysis division of Abbott Laboratories designed to detect chromosomal abnormalities associated with the development and progression of bladder cancer by detecting aneuploidy for chromosomes 3, 7, 17, and loss of the 9p21 locus via fluorescence in situ hybridization in urine specimens from persons with hematuria suspected of having bladder cancer. The UroVysion Kit consists of a four-color, four-probe mixture of DNA probe sequences homologous to specific regions on chromosomes 3, 7, 9, and 17. The UroVysion probe mixture consists of Chromosome Enumeration Probe (CEP) CEP 3 SpectrumRed, CEP 7 SpectrumGreen, CEP 17 SpectrumAqua and Locus Specific Identifier (LSI 9p21) SpectrumGold.

To overcome the laborious process of manual microscopy, a number of researchers, including the present inventors, have proposed automated microscopy systems for capturing and analyzing multiple image views of a biological sample on a microscope slide or other sample retaining device (such as a multiple well plate). Such systems have the potential to greatly improving the efficiency of microscopic analysis and to remove some of the subjective inputs that affect microscopic analysis of a sample.

A number of difficulties are associated with automated microscopy. For example, many of the functions performed in manual microscopy are dictated by undefined methodologies under the control of the human eye and brain. Each of these functions needs to be addressed to allow for the slide to be reviewed with the required clarity. Further, much of the analysis undertaken in traditional manual microscopy involves human reasoning based upon a prior experiences. For example, microscopists are often able to discern an artifact or mistreated sample portion from an actual biological structure, yet have difficult expressing the basis for such decision when asked to set forth the same in words. Further automated microscopy entails the automated device having the ability to handle the slide, interpret the biological structure which is to be investigated and the protocol by which interpretation is to be performed, adjust the slide with respect to the objective, search numerous areas on the slide for such biological structure, determine areas on the slide in which structures of interest reside, process desired signals from structure from extraneous signals, interpret signals, etc.

The present inventors have recognized these and related needs in implementing automated microscopy of a plurality of samples, such as may be used in high throughput microscopic analysis, and addressed these needs herein.

SUMMARY OF INVENTION

In embodiments there is included:

First, a method of microscopic analysis comprising (a) providing an automated microscope comprising a slide stage, at least one objective lens, image capturing means, programmable means for operating the microscope according to a protocol, and programmable means for providing an analytical outcome;

(b) providing a microscope slide containing a sample and interrogatable data thereon, wherein the interrogatable data provide information related to a protocol for analysis of said sample;

(c) interrogating the data;

(d) positioning the slide on the slide stage;

(e) causing the microscope to analyze the sample in accordance with the analytical protocol encoded in the interrogatable data; and (f) causing the microscope to provide an analytical outcome representing the sample.

Second, a method for high throughput microscopic analysis comprising (a) providing an automated microscope comprising a slide stage, at least one objective lens, at least one slide cassette containing at least one microscope slide therein, programmable means for operating the microscope according to a protocol, and programmable means for providing an analytical outcome;

(b) providing a plurality of microscope slides each containing a sample and interrogatable data thereon, wherein the plurality of slides is contained in one or more of said slide cassettes, wherein the interrogatable data provide information related to a protocol for analysis of said sample;

(c) transporting a first cassette into a position suitable for transporting a slide to said microscope stage;

(d) transporting a first slide from the first cassette to said microscope stage;

(e) interrogating the data found on said first slide;

(f) positioning said first slide on the slide stage;

(g) causing the microscope to analyze the sample on said first slide in accordance with the analytical protocol encoded in the interrogatable data;

(h) causing the microscope to provide an analytical outcome representing the sample on said first slide;

(i) if there remains another slide to be analyzed in said first cassette repeating steps (d) to (h); and (j) if there remains another cassette repeating steps (c) to (i).

Third, a computer-readable storage medium tangibly embodying a program of instructions executable by a computer for a method of microscopic analysis using an automated microscope comprising a slide stage, at least one objective lens, image capturing means, programmable means for operating the microscope according to a protocol, and programmable means for providing an analytical outcome; wherein the program comprises a) a set of instructions for interrogating data on a microscope slide wherein the interrogatable data provide information related to a protocol for analysis of a sample included on said slide;

b) a set of instructions for positioning the slide on the slide stage;

c) an analyzing set of instructions for causing the microscope to analyze the sample in accordance with the analytical protocol encoded in the interrogatable data; and d) a set of instructions for causing the microscope to provide an analytical outcome representing the sample.

Fourth, a computer-readable storage medium tangibly embodying a program of instructions executable by a computer for a method of high throughput microscopic analysis wherein the method uses an automated microscope comprising a slide stage, at least one objective lens, at least one slide cassette containing at least one microscope slide therein, programmable means for operating the microscope according to a protocol, and programmable means for providing an analytical outcome; wherein the program comprises a) a set of instructions for transporting a first cassette into a position suitable for transporting a slide to said microscope stage;

b) a set of instructions for transporting a first slide from the first cassette to said microscope stage;

c) a set of instructions for interrogating data on a microscope slide wherein the interrogatable data provide information related to a protocol for analysis of a sample included on said slide;

d) a set of instructions for positioning the slide on a slide stage;

e) an analyzing set of instructions for causing the microscope to analyze the sample in accordance with the analytical protocol encoded in the interrogatable data;

f) a set of instructions for causing the microscope to provide an analytical outcome representing the sample;

g) a set of instructions for determining whether there remains another slide to be analyzed in said first cassette and if so repeating the instructions in (b) to (f); and h) a set of instructions for determining whether there remains another cassette and if so repeating instructions in (a) to (g).

Fifth, a method comprising obtaining a slide containing electronically interrogtable data recorded therewith and having a biological sample thereon;

reading said electronically-interrogatbele data from said slide;

determining from said electronically-interrogatbale data how said biological sample is to be scanned by an automated microscope;

scanning with a automated microscope said slide in the manner dictated by the electronically interogatable data recorded therewith; and determining from said scans a testoutcome indicative of a state of said biological sample.

BRIEF DESCRIPTION OF THE DRAWINGS

FIG. 9 provides a flow chart giving details of steps in an embodiment of the invention.

DETAILED DESCRIPTION OF THE INVENTION

Figure 1:
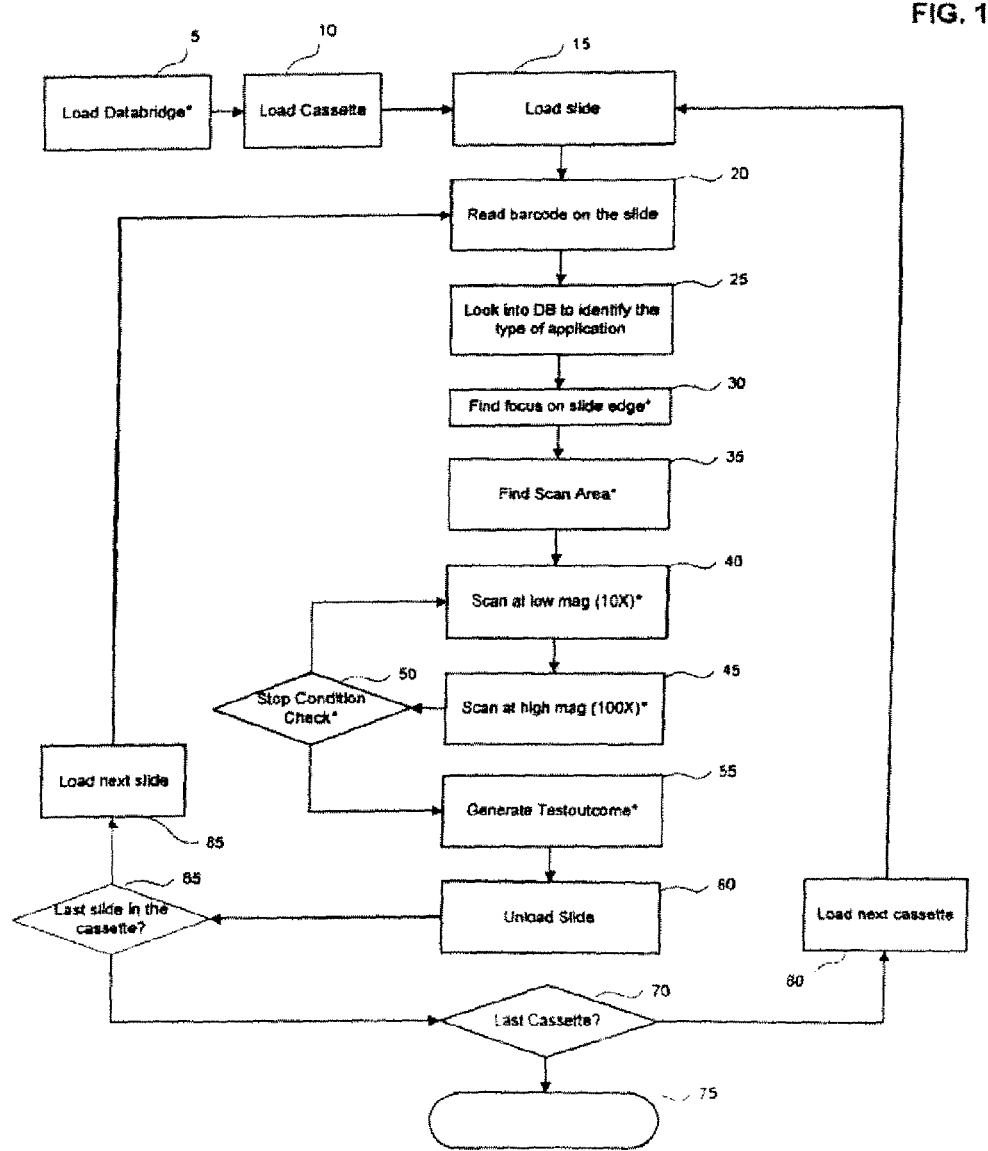
FIG. 1 provides a flow chart giving an overview of steps in an embodiment of the invention.

Turning to FIG. 1, there is disclosed a master diagrammatic flow chart of an embodiment of the present invention. FIG. 1 presents an overview of the various computational modules that together implement the automatic retrieval and analysis of samples on multiple slides. Such a collection of slides may arise in a research setting or in a diagnostic setting. Large numbers of slides are advantageously examined and analyzed by the automated methods disclosed herein. Biological specimens, cellular or tissue preparations, and similar subjects of investigation constitute nonlimiting examples of subjects for microscopic analysis by methods of the invention. These are generally termed "samples" or "specimens" herein. Commonly the samples include labels to assist in microscopic analysis. Frequently such labels are fluorescent labels. A sample may furthermore include more than one fluorescent labels, wherein each label has particular and distinguishable fluorescent properties, esp. distinguishable excitation and emission wavelengths. In order to conduct suitable microscopic analysis of such samples, appropriate excitation filters are placed in the light beam illuminating the sample, or one of a plurality of laser sources of differing wavelengths is chosen, and corresponding emission filters are placed between the sample and an image capture device such as a camera or charge coupled detector (CCD). In a procedure governing automated microscopic analysis of such samples, a computer or similar controlling device must have available information describing the nature of the probes to be examined. Sample identification including this requisite information, as well as additional sample identifiers, may be encoded on each slide using an interrogatable coding means, such as a barcode or barred array. The interrogatable coding is read as a slide is positioned in the microscope, and the corresponding information is communicated to the computer or controlling device.

As seen in FIG. 1, the analysis for a particular slide, once loaded in place onto the stage of a microscope (15), begins by reading a barcode present on the slide (20). The barcode include information designating the nature of the microscopic analysis to be carried out. The details for the diverse analytical protocols are stored in a database for reference by the computer or controlling device. Once the slide barcode is read, the correct experimental protocol is identified in a database (DB) according to the information encoded in the barcode (25). With this information now available to control the operation of the microscope, a concatenated series of operations that regulate the focusing, optimize the region on the slide to be scanned to provide a suitable image, including adjustments for low magnification to start with, and moving to a higher magnification for the actual analysis, is carried out (see steps 30, 35, 40, 45, and 50). A successful implementation of the various modules involved in this protocol provides results, designated a "Testoutcome" in FIG. 1 (55). The remaining loops illustrated in FIG. 1 relate to determining whether, in a given cassette, the last slide in the cassette has been examined (65 and 85); and whether slides in the last cassette have been analyzed (70 and 80). When the last cassette has been examined, the operation of the microscope ceases (75).

Figure 13:
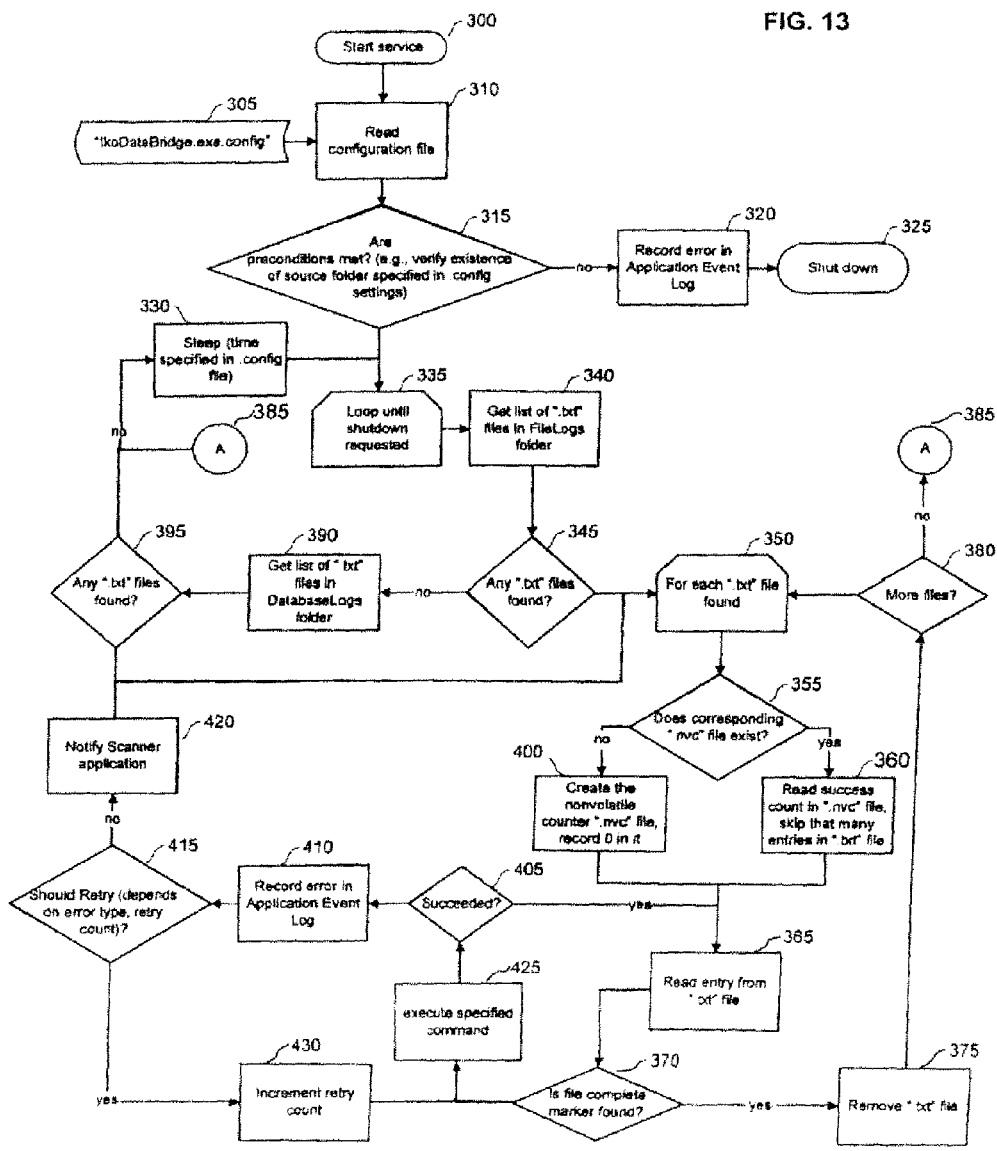
FIG. 13 provides a flow chart giving details of steps in an embodiment of the invention.

As indicated at FIG. 1, the databridge application is started (step 5) to run as a system service for file handling in parallel with other process that may be running. Such service may be a method such as shown at FIG. 13, wherein the service is started (step 300) which might include setting parameters and the environment in which the application will run. In the method of FIG. 13, a configuration file is read (step 310) such as may be provided by IKoDataBridge.exe.config (step 305). If preconditions are not met an error is recorded in a file, such as an application event log (step 320) and the process shut down (step 325). If preconditions are meet (step 315) such as the existence of source folders, a loop is performed (step 335) until a shut down is requested. Starting the loop a log file is queried for a list of files (step 340), for example ".txt" files. If files are found (step 345) another loop is started (step 350) wherein a further check is performed for a corresponding file, such as a ".nvc" type file. Existence of the corresponding file would then lead to a read of success counts within such a ".nvc" file and cause a skip of entries in the original file (step 360). After reading of the entry from the original file, for example the ".txt" file (step 365) a query is performed as to whether the complete marker is found (step 370), whereupon the text file would be removed (step 375). Interrogation of more files is made (step 380), resulting in a return and continuation of the loop initiated for each file found, such as a ".txt" file (step 350). If more files are not found (step 380) the system, as illustrated by the alternative path (step 385, 385'), is put to sleep based on the time specified, for example in a configuration file such as ".config" (step 330). Completion of the sleep period (step 330) results in return and continuation of the shutdown loop starting (step 335). Failure of finding the complete marker in step 370 will trigger a specific command in step 425 to execute. If the execution is successful (step 405) the reading of an entry from, for example, a ".txt file" is resumed as seen in step 365. Non success at step 405 in executing the command of step 425 records an entry into a log file, such as an application event log(step 410), query of the error type and count (step 415) and possible increment of a retry count at step 430, returning to the execution step of 425. A sufficient error or retry count of commands, as tested at step 415 may result in a notification to a scanner application as in step 420 and return to step 350 for continue to loop for another file, such as ".txt" file. In the event a corresponding file, such as a ".nvc" file does not exist (step 355), a file will be created containing a zero (step 400), where after the process will occur as performed above continuing from step 365. The absence of found files at step 345 would cause a retrieval of a file list from a folder, for example a databaselog folder (step 390), and query of the list in step 395 for files. If no files are found the service would be placed in sleep mode as shown in step 330, or if files were found the process would return to the file loop at step 350.

Turning back to FIG. 1, slides having bar coded or other electronically-readable indicia are loaded into a cassette (step 10) having multiple slots from which such slides may be obtained. A slide for analysis is then loaded (step 15) into an automated microscope. The barcode or other electronically-readable indicia is read (step 20) to determine the type of processing demanded (e.g., type of application demanded) on the slide by reference to a database (step 25). The automated microscope then seeks to execute a number of steps to detect objects of interest in the sample based on the processing demand.

Figure 7:
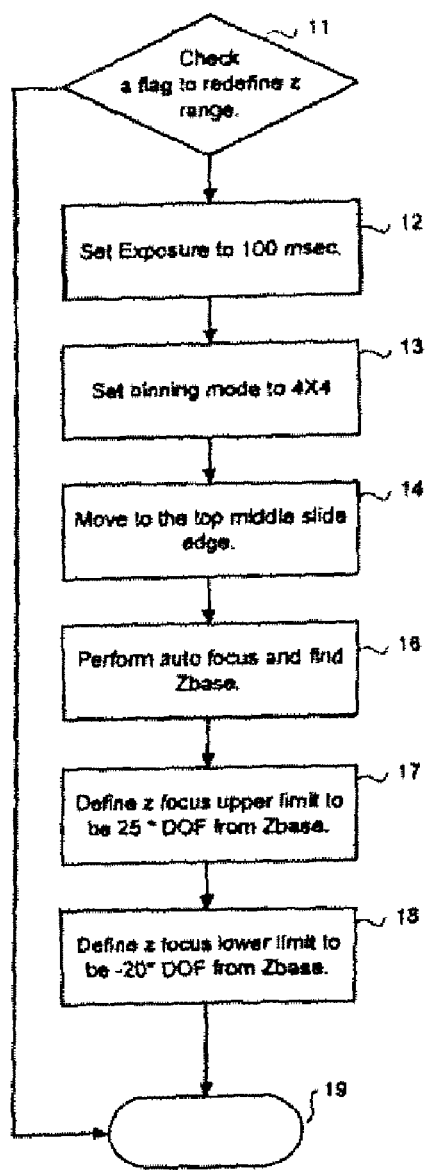
FIG. 7 provides a flow chart giving details of steps in an embodiment of the invention.

First the sample is focused with respect to the objective. Focusing may be transacted by using a known reference point, such as the slide edge (step 30) from which focus may be effectuated. Such focusing may be a method such as shown at FIG. 7 wherein depth of focus in the z range is redefined if certain parameters raise a flag of out-of-focus situation (step 11) or not (step 19 termination). In the method described at FIG. 7, the slide is exposed to an interrogation for a period of time, for example 100 msec (step 12), with the binning mode being set to cover a substantial area, for example set to 4×4 (step 13). The interrogation spot is then set to a reference point on the slide edge, such as the top middle slide edge (step 14). Autofocus is then performed to determine a Zbase (step 16), that is, a base point along the Z axis, such as at the top surface of the slide edge. From the Zbase a z-focus upper limit is defined (step 17), such as 25 times the depth of focus from the Zbase, and a z-focus lower limit is defined (step 18)

Figure 2:
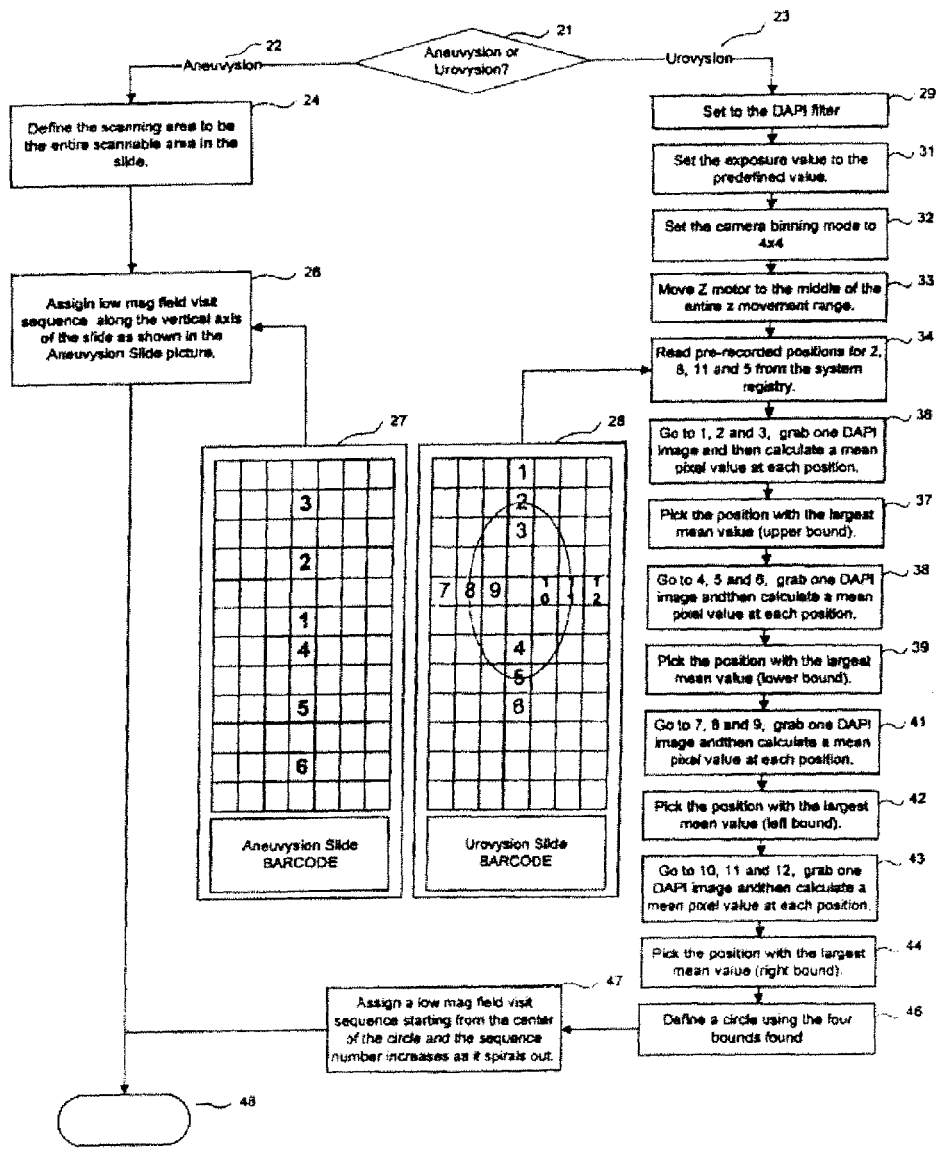
FIG. 2 provides a flow chart giving details of steps in an embodiment of the invention.

Returning to FIG. 1, after focusing, the scan area is determined (step 35) based upon a predetermined algorithm. For example, FIG. 2 shows two different schemes for scan area definition based upon two different FISH-based tests, AneuVysion (22) and UroVysion (23) based on bar coded or other electronically-readable indicia on the slides (step 21). Such tests differ in the manner of applying the sample, with the AneuVysion sample being placed in smear on the slide, and the sample applied to a UroVysion Slide a dropped blob.

As illustrated at FIG. 2, if an AneuVysion test (22) is indicated, the scanned area is defined at step 24 as being the entire scannable area on the slide to determine the position of a smear on the slide. As illustrated, low magnification field visits ("survey visits") are made for rapid detection of possible candidates according to a sequence along the vertical axis of the slide (step 26), for example, in a pattern as set forth at 27. Query of isolated possible candidates may then be performed by high magnification ("investigation mode").

As further shown in FIG. 2, with respect to UroVysion slide 28 investigation of possible candidate may employ numerous steps. At step 29, a filter is set to selectively determine fluorescent signals from a label such as DAPI interacting with the sample. Exposure value is set to a predefined value at step 31, and the binning mode (merging of distinct pixels) of the camera set to a predefined level, such as 4.times.4 (step 32), to allow for expeditious scanning of the slide. The Z-motor is then positioned to allow for fixed z-position reading of locations on the slide, for example, set to the middle of the entire z-movement range (step 33). Read is made of pre-recorded positions on the Urovyision Slide 28, for example, as illustrated 2, 8, 11, and 5 of the registry (step 34). Interrogation is made of pre-programmed location field on slide 28, such location field for example, encompassing positions 1, 2 and 3 (36), with imaging being made of the DAPI signals at such pre-programmed filed and a mean pixel value at each position being determined at step 36). At step 37 the position with the largest mean pixel value (upper bound) is selected for each pre- programmed location field, as reiterated at steps 38/39, 41/42 and 43/44. Using the positions identified as having the largest mean pixel value, a enclosed boundary is defined (step 46). Within such defined enclosed boundary there is then assigned a low magnification yield visit sequence starting form the center of the defined boundary (for example, circle) with the sequence number increasing as one spirals out (step 47).

Turning back to FIG. 1, a low magnification scan is then performed at step 40. Such low magnification scan may entail discrete steps as set forth at FIG. 3. At step 49 magnification is set to a low value, for example, to an objective lens having 10× magnification. Quality control measures, such as Objective repeatability, or other forms of quality checks may then be determined at step 51, using methodology, for example, as set forth at FIG. 5.

Figure 5:
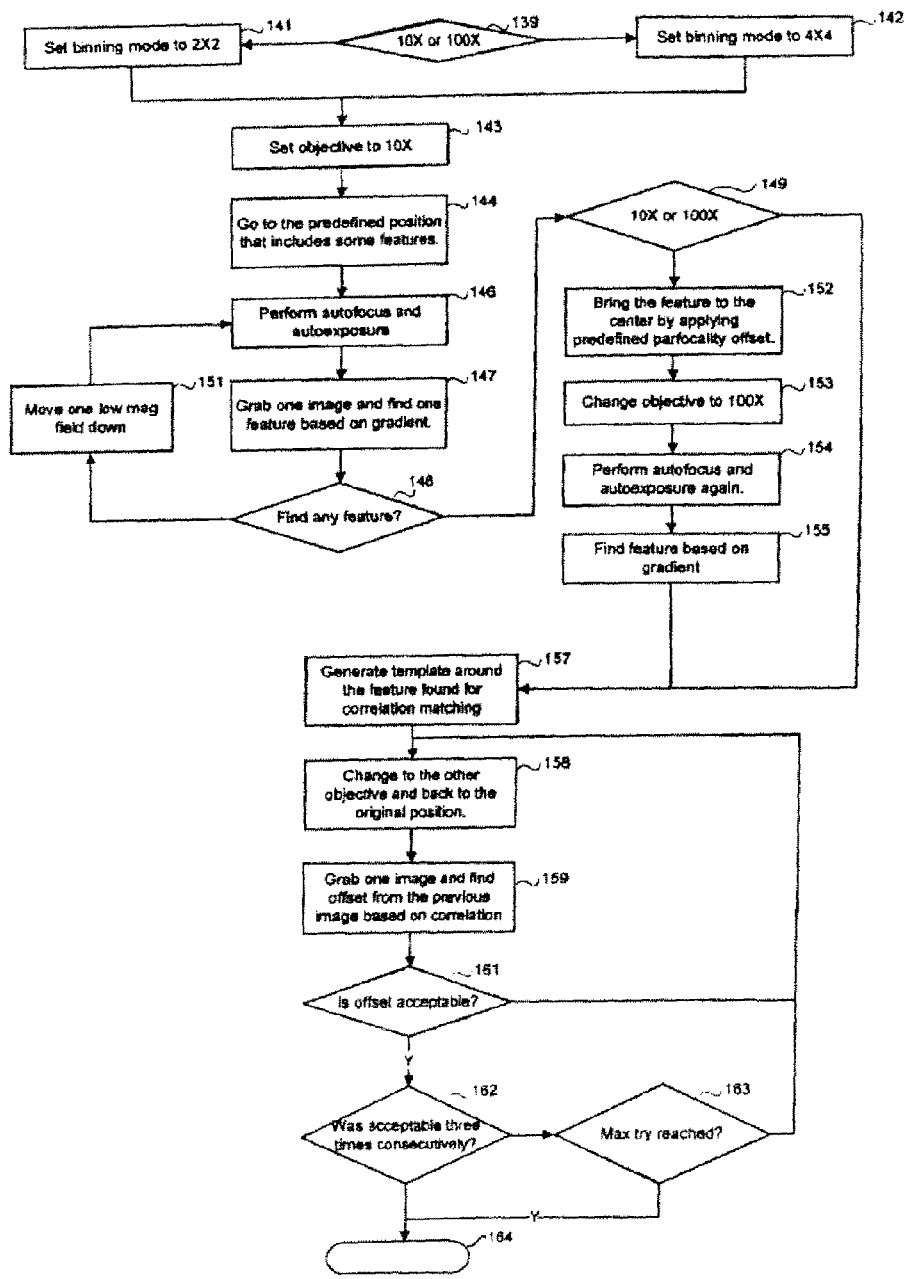
FIG. 5 provides a flow chart giving details of steps in an embodiment of the invention.

Objective repeatability may be determined using the embodiment methodology as shown at FIG. 5. First, binning mode is set for each magnification level (for example, 10× or 100× as set forth at 139) which will be used to scan the scan area. For example, binning mode may be set to 2×2 (141) or alternatively 4×4 (142) as shown in FIG. 5. With the objective set to the appropriate magnification, e.g., 10× as set forth at 143, the interrogation is sent to a predefined position that has been determined to include some features of potential interest 144. Autofocus and autoexposure are performed (step 146) with one image grabbed and at least one feature is identified as, for example, by determining a gradient, such as an optical gradient (step 147). If a feature is not determined at step 148 the low magnetic field is lowered more and autofocus and autoexposure of step 146 is repeated. If a feature is determined at step 148 the magnification is verified at step 149, features of interest are centered applying a pre-defined parfocality offset (step 152) and the objective magnification changed, as for example, to 100× as at step 153. Again, autofocus and autoexposure are performed (step 154) and a gradient used to find the feature of interest (step 155). A template may then be generated around the feature isolated for correlation matching (step 157). The objective is then changed once more to the original objective and position, the image is grabbed and the offset determined from the previous image based on correlation (step 159). If the offset is acceptable (step 161) and offset is acceptable multiple consecutive times, such as, three times (step 162) the objective repeatability test is terminated (step 164). If acceptability does not reach offset acceptability in a consecutive predetermined maximum number of attempts (step 163) then there is change of the objective back to the original position (step 158). If a feature is not found at 148, then there may be a move down of one low magnification field (151) and the path continued at step 146.

Turning back to FIG. 3, after objective repeatability is confirmed at step 51, an image processing thread is created (step 52). As a simultaneous process, the image processing thread is first initialized (step 73), and images saved (step 76) after waiting for image processing jobs in the queue (step 74). The images are then processed and in accord with an algorithm candidate nuclei are selected and x-y positions of each candidate nuclei target are determined (step 77). From the x-y positions determined, the interrogation strategy is set based on the high magnification to be used, so as to maximize the number of nuclei per field and minimize the total number of high magnification fields necessary to visit such nuclei candidates (step 78). A determination is made upon receipt of images whether the thread should be terminated (step 79), if not image processing continues (step 74), and if termination is determined (step 81), then based on the test screening protocol, for example, as illustrated, Aneuvysion or UroVysion (step 83), the fields are sorted in a manner to provide required information. For example, with respect to an AneuVysion test (step 82), the list of high magnification fields may be sorted based on a number of nuclei in the filed (step 86), and with respect to a UroVysion test (step 84), the list of high magnification fields may be sorted on largest nucleus size in the field (step 87), followed by termination (step 88).

Figure 3:
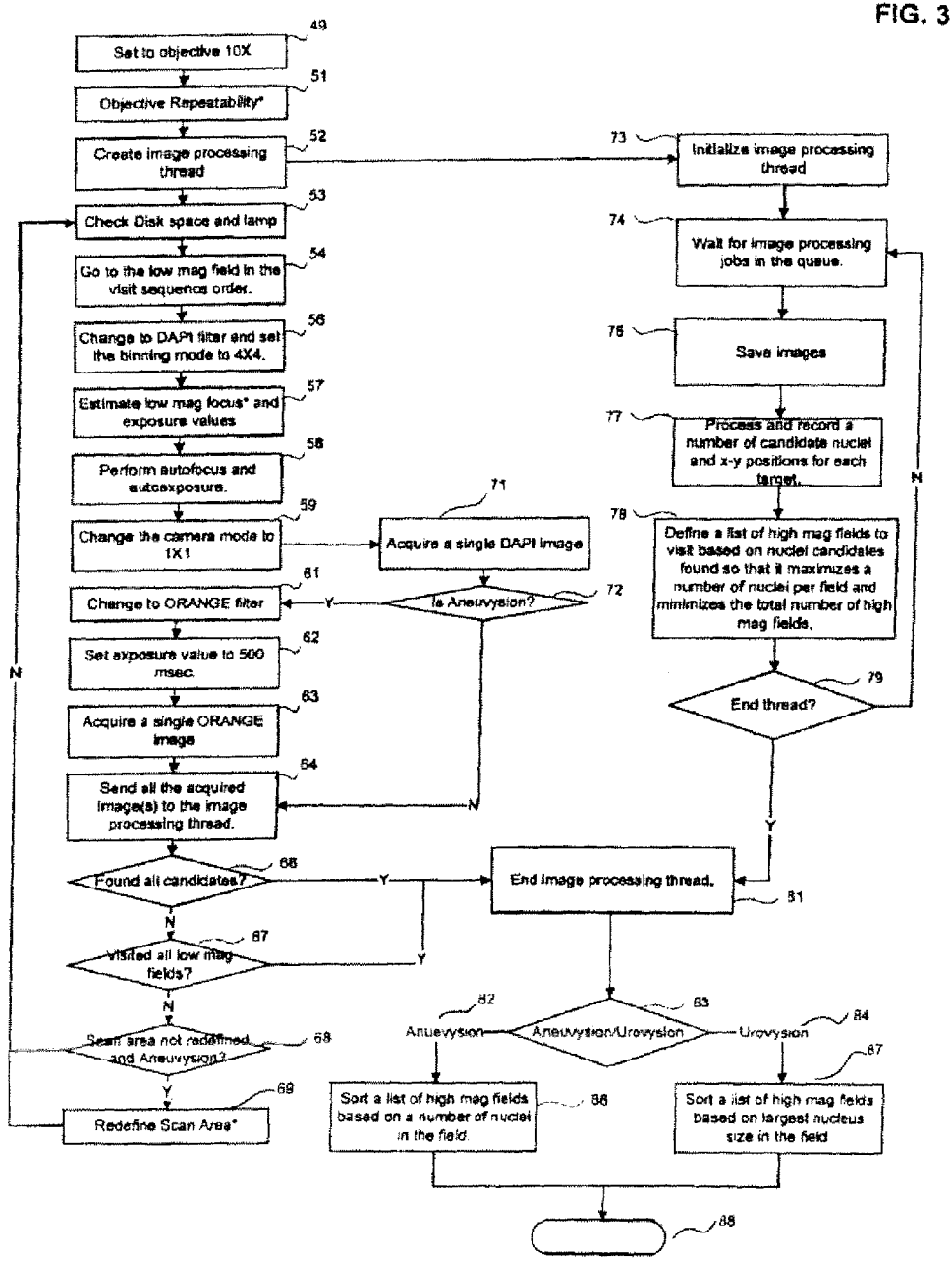
FIG. 3 provides a flow chart giving details of steps in an embodiment of the invention.

Now turning to step 53 of FIG. 3, after creating the image processing thread (step 52) as discussed above, the system is set for acquiring images. First parameters necessary for imaging are checked, for example, disk space and activating source (e.g., lamp). The sample is then visited with a low magnification field search in the predetermined visit sequence order (step 54). In conjunction, filters may be effectuated, for example a DAPI filter for determining nuclear tags, and the binning mode adjusted for appropriate resolution (step 56). The low magnification objective lens is then adjusted for focus (step 57), for example, by a methodology such as described at FIG. 10.

Figure 10:
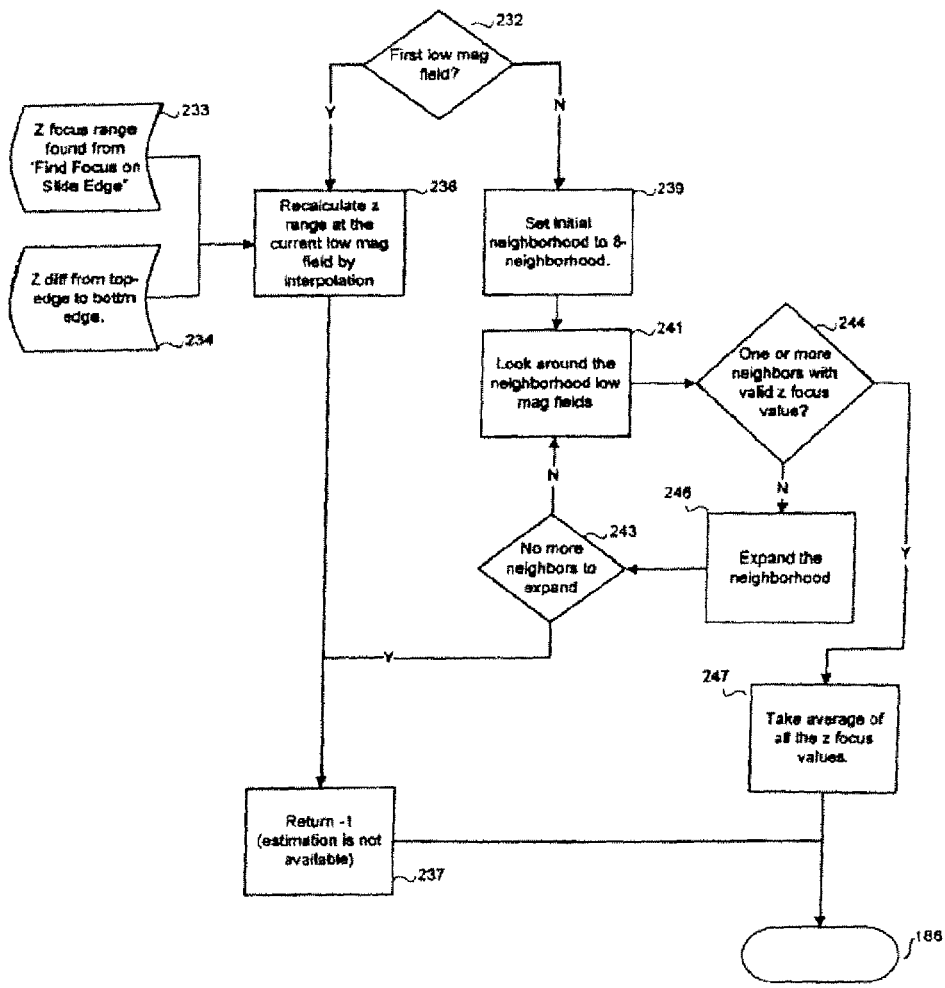
FIG. 10 provides a flow chart giving details of steps in an embodiment of the invention.

In FIG. 10, there is shown a method for adjusting low magnification focus. First there is a determination of whether the low magnification field is the first low magnification field in the sequence order (step 232). If the low magnification field is the first low magnification field in the sequence order at step 236 the z-range at the low magnification field is recalculated by interpolation using database(s) incorporating z-focus range found from the "find focus on slide edge" (233) and z-difference from the top edge to bottom edge (234) if possible if not (step 237) there is termination (step 186). If the low magnification field is not the first low magnification field in the sequence order, then the neighborhood of potential structures of interest is set to a defined number (step 239) and each neighborhood is inquired in low magnification (step 241) to determine if there is one or more neighborhoods with a valid z focus value (step 244), and if so, the average of all the z focus values is taken (step 247), and if not, the number or size of neighborhoods are expanded (step 243) until there are no more neighbors to expand (243), and a flag (237) is sent to complete (186) the string.

Returning back to FIG. 3, at step 58 autofocus and autoexposure are performed The binning mode may then be changed (step 59), for example, to 1×1 as illustrated, an image, for example a DAPI image (step 71), acquired. Depending on the test used to elucidate objects of interest, such as, for example, an Aneuvyision test (72), one may need to alter other microscopic parameters to elucidate such objects. For example, there may be need to alter filtering (step 61) of emanating signals from the sample, and change the exposure value of the sample (step 62). Once an image is acquired (step 63) it may be processed using the processing thread discussed supra (step 64) and once all candidates are located (step 66), and each of the fields interrogated (step 67), the imaging process thread is terminated (step 81).

Depending upon the test protocol used (e.g., AneuVysion or UroVysion 82, 83, 84), the processed images are handled in a predetermined manner, for example, with respect to an AneuVysion test by sorting the list of high magnification fields based on the number of nuclei in a field (step 86) and with respect to a UroVysion test, sorting the list of high magnification fields on the basis of the largest nucleus size in the field (step 87). If all candidates are not located (step 66), and each of the fields is not interrogated (step 67), and the scan area may be redefined (steps 68, 69).

Figure 8:
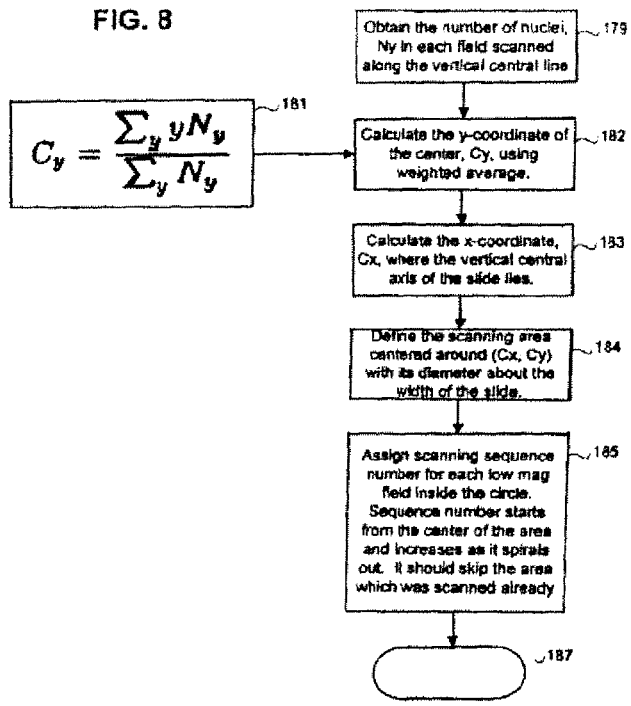
FIG. 8 provides a flow chart giving details of steps in an embodiment of the invention.
Figure 14:
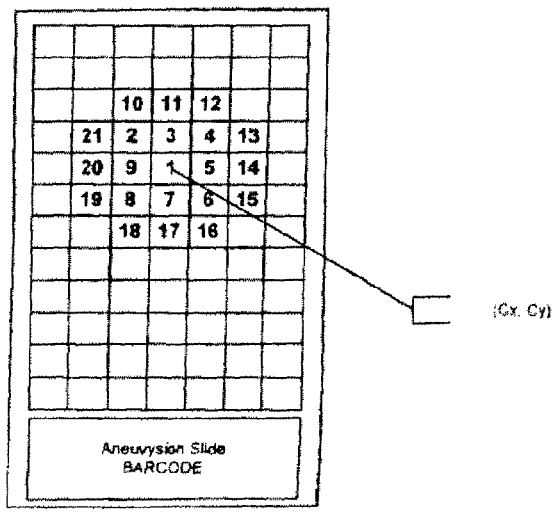
FIG. 14 is a schematic representation of a scanned area using a spiral scanning technique, according to an embodiment related to FIG. 8.

Redefinition of the scanner area may be by the methodology of FIG. 8 wherein a central point is selected from which spiral scanning techniques such as in the order set forth in FIG. 14 are performed. Such spiral scanning may be defined by the equation of step 181. In such methodology, at step 179, obtain the number of nuclei, Ny, in each field scanned along the vertical central line. At step 182, calculate the y-coordinate of the center, Cy, using weighted average. Subsequently at step 183, calculate the x-coordinate, Cx, where the vertical central axis of the slide lies. Then at step 184, define the scanning area centered around (Cx, Cy) with its diameter about the width of the slide. Finally at step 185, before termination (step 187), assign scanning sequence number for each low mag field inside the circle. Sequence number starts from the center of the area and increases as it spirals out. It should skip the area which was scanned already.

Once the low magnification scan area is defined (step 35 of FIG. 1) and the sample is scanned at low magnification (step 40 of FIG. 1), a scan at high magnification may be performed (step 45 of FIG. 1).

Figure 4:
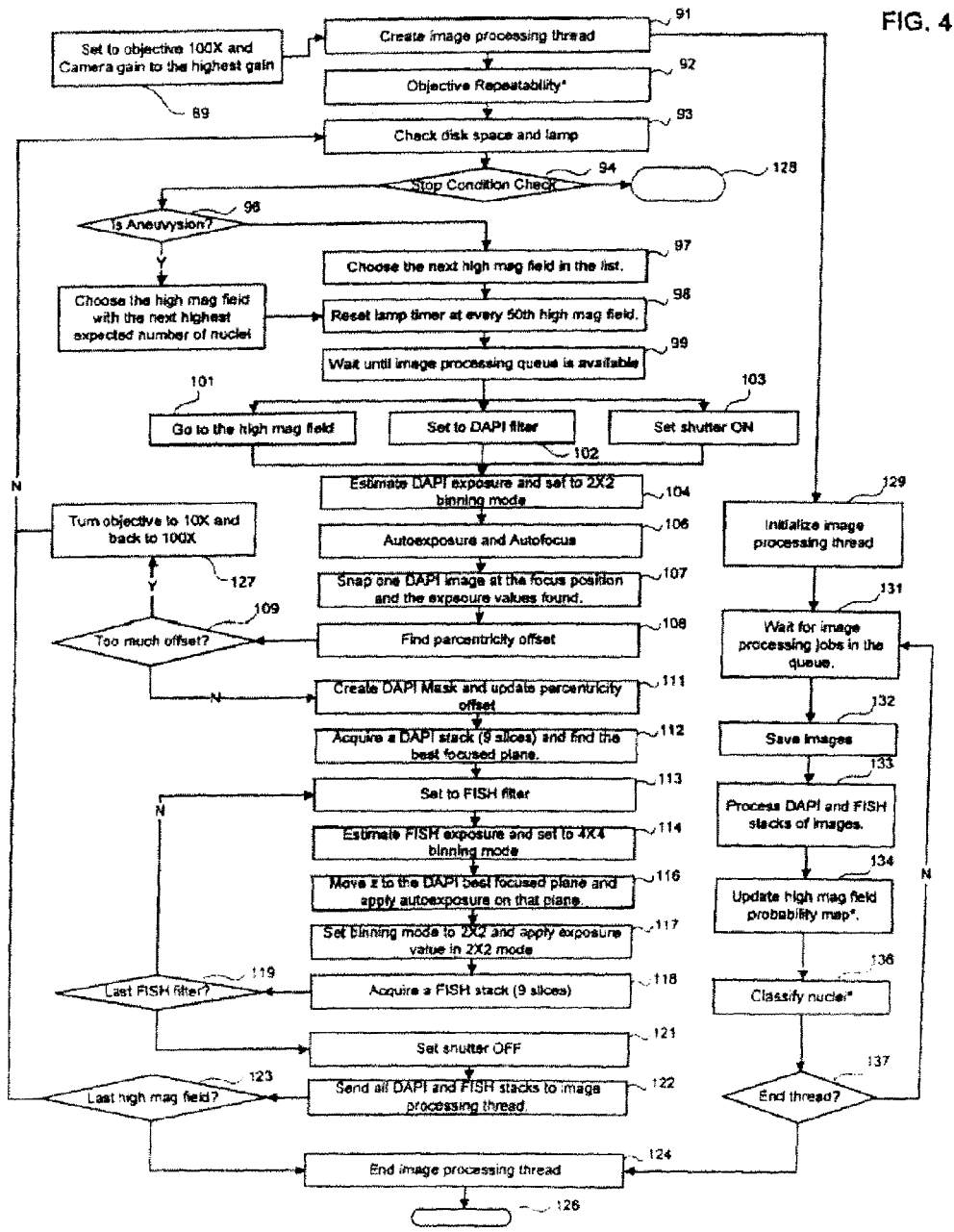
FIG. 4 provides a flow chart giving details of steps in an embodiment of the invention.

High magnification scanning may employ a methodology such as portrayed at FIG. 4. The objective is set to high magnification, and camera gain set to highest gain (step 89).

Figure 12:
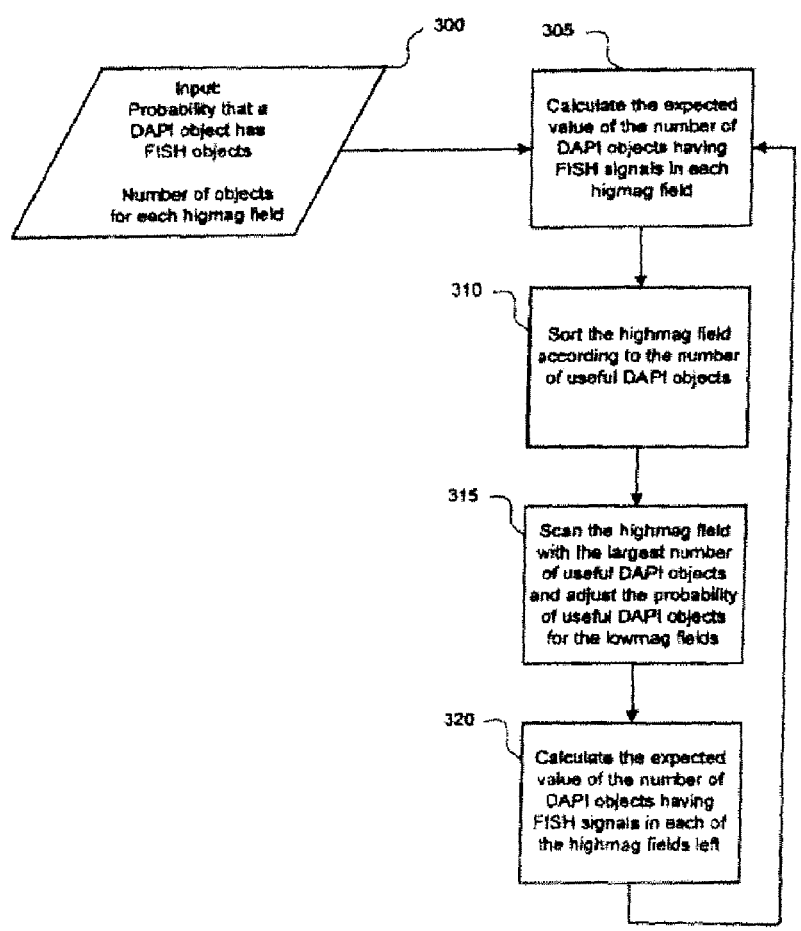
FIG. 12 provides a flow chart giving details of steps in an embodiment of the invention.

The imaging processing thread for high magnification is then created (step 91) by first initialization (step 129), waiting for image processing jobs in the queue (step 131), saving the image (step 132), processing image stacks (step 133) (such as DAPI and FISH images), updating the high magnification field probability map (step 134), classifying the targets of interest (step 136), e.g., nuclei, and finally ending the thread if appropriate (steps 137/124) and continuing at 126. The updating of the high magnification field probability map of step 134 may be by a method as set forth in the flow chart set forth at FIG. 12.

As shown, at step 300, there is provided input as to the probability that a object (such as a DAPI object) has other objects of interest associated (such as FISH objects) and input pertaining to the number of objects for each high magnification field. Next there is calculation of the expected value of the number of signals of interest having other objects of interest associated therewith (step 305) such as DAPI objects having Fish Signals, in each high magnification field. The high magnification fields are then sorted (step 310) according to the number of useful objects, such as DAPI objects. (step 310), the high magnification fields with the largest number of useful objects, such as DAPI objects, are scanned and the probability of useful objects, such as DAPI objects, for the low magnification fields are adjusted (step 315). The expected valve of the number of objects having a desired signal (e.g. DAPI objects having FISH signals) in each of the high magnification fields are calculated at step 320.

For example, the high magnification field probability map with respect to DAPI objects having FISH signals may be determined. DAPI objects for high magnification scanning may be sorted based on the number of objects contained in the high magnification field in order to reduce the number of fields to be scanned to find enough useful DAPI objects within the least amount of time. DAPI objects having good FISH signals (i.e. objects containing the most number of useful DAPI objects) may be further sorted to reduce the time necessary of high magnification analysis. Assuming the probability for a high magnification field being properly processed to have FISH objects to be $p=m/n$, every time a DAPI object is found to contain FISH objects, the probability can be addressed to be $p=(m+1)/(n+1)$. Every time a DAPI object is found to contain FISH objects, adjust the probability to be $p=m/(n+1)$. The expected value of the number of useful objects in each high magnification field is then the multiplication of the number of DAPI objects and the probability. The high magnification field with the largest expected value of the number of objects may be chosen to be scanned. Note that, the value of p can be obtained statistically by experiments on typical slides. With a fixed p, the value of m (or n) needs to be carefully chosen so that each object, no matter it has FISH signals or not, can have a proper impact factor on the probability adjustment.

The pseudo code of an algorithm for a DAPI/FISH system that may be used is set forth below:

1. Let the initial lowmag field quality indicator be $p_i=m_i/n_i=p=m/n$.
2. Calculate the expected value of the number of objects in each himag field and sort them.
3. Choose the himag field with the largest expected number of objects.
4. If the expected number of objects is less than $N_{min}$, stop.
5. Scan and analyze the himag field chosen.
6. For each object in the himag field, decide if it contains FISH signals. Let $n_i=n_i+1$. If the object contains FISH signals, then $m_i=m_i+1$.
7. If enough useful DAPI objects have been found, stop.
8. Calculate the new field quality indicator $p_i=m_i/n_i$.
9. Update the expected value of the number of objects based on the field quality indicator in the remaining himag fields within the current lowmag field.
10. Sort the remaining himag fields and go to 3.

By choosing appropriate values from m and n, one can achieve a large variety of scanning strategies. For high magnification scanning application, it may be desired that the algorithm be able to abandon the field where there are objects without FISH signals. To do so, one may choose small values for m and n (for example, in =1, n=2; or if one wants to abandon fields faster, in m=0.5, n=1). The $N_{min}$ may be chosen, for example, to =0.2~0.3.

Figure 11:
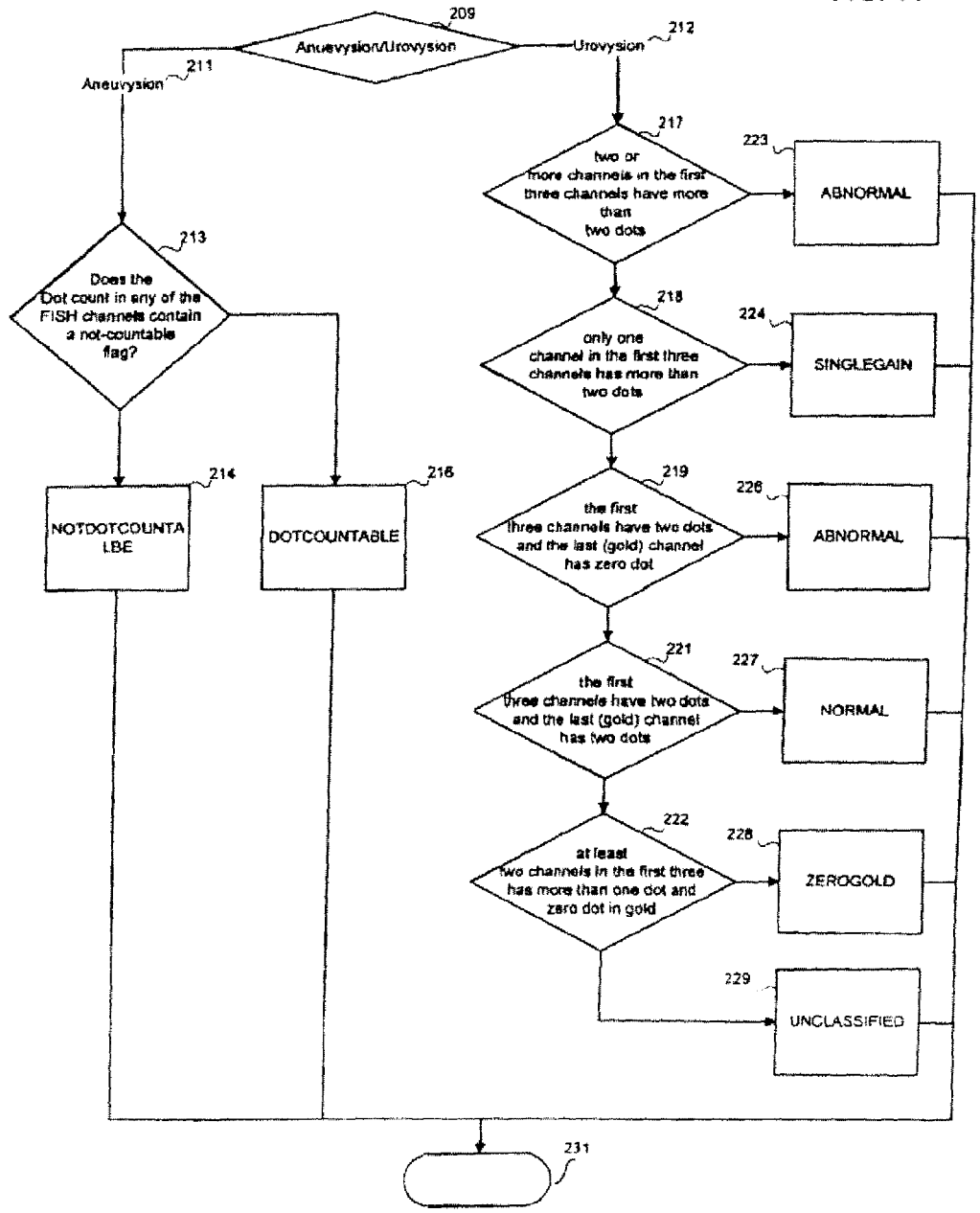
FIG. 11 provides a flow chart giving details of steps in an embodiment of the invention.

In respect of the classification of nuclei at step 136, classification may be directed by the particular testing protocol being employed, such as, for example, AneuVysion/UroVysion (209, 211, 212) of FIG. 11. For example, when nuclei on a AneuVysion test slide are being counted, a simple determination of whether the dot count in any of the FISH channels does not contain a countable flag (step 213) may be used to determine whether the proposed nuclei dot should be counted (216) or not counted (214). Similarly, when nuclei on an UroVysion test slide are being counted, channel count may be used in respect to classification of the nuclei. For example, if two or more channels in a plurality of channels, for example three channels, have more than two dots (217), then an abnormal classification (223) may be given, or the first three channels have two dots and the last (e.g. gold) channels has zero dots (219), a classification of abnormal (226) may be given, while if the first three channels have two dots and the last (e.g., gold) channel has two dots (221), then a classification of normal (227) may ensue. If only one channel in the first of the plurality of channels has more than two dots (218) then the classification may be singlegain (224), while if at least two channels in the first three channels has more than one dot and zero dot in gold (222), then a classification of zerogold (228) or unclassified (229) may be rendered. Upon classification of each nuclei the classification process may be terminated (231).

A scan at high magnification (step 45 of FIG. 1) employing the methodology as set forth at FIG. 4, after creation of the image processing thread (step 91) may transact an object repeatability test (92), for example, as discussed with respect to FIG. 5 supra. Again parameters of the microscope such as disk space and lamp (step 93) may be performed and the stop condition checked (94).

Figure 6:
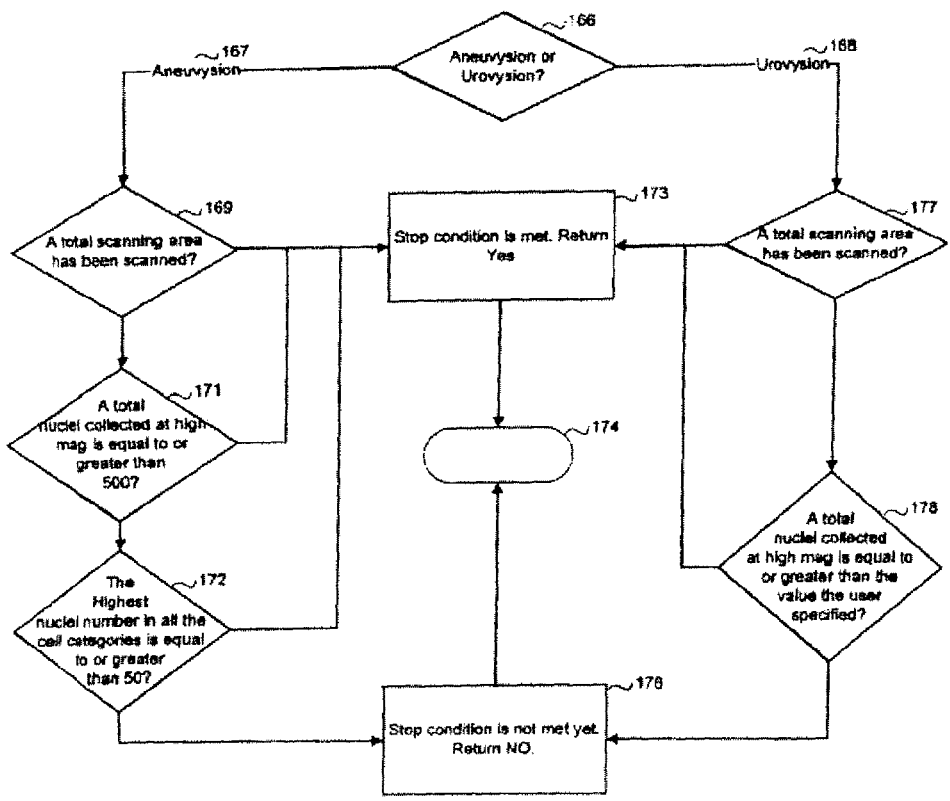
FIG. 6 provides a flow chart giving details of steps in an embodiment of the invention.

Stop condition checking (94) may depend on the particular testing protocol being employed, for example, AneuVysion or UroVysion (166, 167, 168; see FIG. 6).

If AneuVysion (167), for example, a determination may be made if the total scanning area has been scanned (169) and if it is so having the stop condition being set (173) and the process terminated (174). On the other hand, if a determination is made that the total scanning area has not been made (169), then the total nuclei collected at high magnification may be compared to a threshold, such as equal to or greater than 500 (171). If this threshold has been met, the stop condition may be determined to be met (173). If the threshold has not been found to be met, and the highest nuclei number in all the cell categories is determined to be above a predetermined minimum threshold (such as equal to or greater than 50) (172), the stop condition may also be determined to have been met (173). If it is below the predetermined minimum threshold, the stop condition may be determined not to have been met (176).

If UroVysion is the particular protocol employed (168), a determination may be made if the total scanning area has been scanned (177), and if so the stop condition being met, and if not another parameter being sued to meet the stop condition (173). For example, one might make as a condition of a stop condition being met (173) that the total nuclei collected at high magnification be equal to or greater than the value the user specified (178) (if not the stop condition is not met 176).

Turning back to FIG. 4, the type of test performed on the sample (for example, AneuVysion (step 96)) may influence the step of high magnification scanning (step 45 of FIG. 1). For example, if AneuVysion is the test (step 96) one might choose the high magnification field with the next highest expected number of nuclei (step 138) for scanning, while if such test was not employed, the next high magnification field in the list (step 97) might be scanned. It may be necessary in the process to periodically adjust parameters of the microscope, for example, resenting the lamp timer at every 50th high magnification field (step 98). Before taking an image it is advantageous to confirm that the image processing queue is available (step 99). Appropriate filters (step 102) may need to be set, the shutter set to on (step 103) and the high magnification field entered (step 101). The exposure time to an appropriate interrogation wavelength may then be estimated with a setting of a binning mode (step 104). After adjusting autoexposure and autofocus (step 106), an image, such as a DAPI image, may be taken at the focus position and the exposure values found (step 107). Parcentricity should be confirmed by determining parcentricity offset (step 108) and if the offset is too much (step 109) the objective turned between low and high magnification (step 127), the check process repeated, or if there is a determination that the last high magnification field has been reached (step 123) the image processing thread terminated (step 124). If the offset is not too much, then other mask may be employed, such as a DAPI mask and the parcentricity offset updated (step 111). After requiring a stack of images, for example nine slices, the best focused plane may be determined (step 112), further filters set (step 113), such as a filter for detecting FISH signals, and exposure time recalculated and binning mode set (step 114). Autoexposure on the best focused plane may be effected (step 116) followed by resetting of the binning mode to a new value and applying exposure (step 117) to obtain a stack of images of the signals to which the filter has been set (step 118), for example FISH signals, until the desired number of filters to produce the stack has been completed (step 119). The shutter of the image obtaining device may then be set to off (step 121), the images obtained sent to the image processing thread (step 122) with the image processing thread being terminated (step 124) after determining the last high magnification field has been queried (step 123). Finishing of the high magnification scan (step 126) upon a stop condition check (step 50 of FIG. 1)—such as described above with respect to FIG. 6, may prompt the automated microscope to generate a testoutcome (step 55 of FIG. 1).

A exemplary automated method for determining a testoutcome (step 55 of FIG. 1) with respect to a Aneuvyision or UroVysion test (188, 189, 191) is set forth at FIG. 9. As depicted with respect to a AneuVysion test (189) each fluorescent taggant (CEP v. LSI) (192) is analyzed with respect to binding with the target chromosomal regions for such taggants. For example, with respect to CEP (193) the X,Y and 18 dotcounts are determined (step 196), and with respect to LSI (194) the dotcounts with respect to chromosomes 13 and 21 are obtained (step 197). The dotcounts determined are then matched (step 198) against a database of possible outcomes for CEP labeling (201) or LSI labeling (202). If the dotcount obtained matches a possible dotcount outcome for valid CEP labeling (201) then the output matched is sent as the testoutcome. However if the dotcount obtained does not match with a possible dotcount outcome for valid CEP labeling (201), then there is a determination if the reason for the failure of the match is due to the analysis of too few nuclei (step 199), and if yes the testoutcome output is sent as "less than 50 nuclei images" (206), and if no the testoutcome is output as "review recommended" (204). Testoutcome is terminated at 208.

Turning back to FIG. 1, after generation of a testoutcome (step 55), the slide having been interrogated is unloaded (step 60) and a new slide from the cassette is loaded (step 85) if the slide is not the last slide in the cassette (steps 65, 70). If it is the last slide in the cassette (step 70) then the next cassette may be loaded if such is available (step 80), or if not the run may be terminated (step 75).

Statement Regarding Preferred Embodiments

While the invention has been described with respect to preferred embodiments, those skilled in the art will readily appreciate that various changes and/or modifications can be made to the invention without departing from the spirit or scope of the invention as defined by the appended claims. All documents cited herein are incorporated by reference herein where appropriate for teachings of additional or alternative details, features and/or technical background.

We claim:
1. A method comprising:
   obtaining a slide containing electronically interrogatable data recorded therewith and having a biological sample thereon;
   reading said electronically-interrogatable data from said slide;
   determining from said electronically-interrogatable data how said biological sample is to be scanned by an automated microscope;
   scanning with an automated microscope said slide in the manner dictated by the electronically interrogatable data recorded therewith; and
   determining from said scans a test outcome indicative of a state of said biological sample.
2. A method of microscopic analysis comprising:
   providing an automated microscope comprising a slide stage, at least one objective lens, image capturing means, programmable means for operating the microscope according to a protocol, and programmable means for providing an analytical outcome;
   providing a microscope slide containing a sample and interrogatable data thereon, wherein the interrogatable data provide information related to a protocol for analysis of said sample;
   interrogating the data;
   positioning the slide on the slide stage;
   causing the microscope to analyze the sample in accordance with the analytical protocol encoded in the interrogatable data; and
   causing the microscope to provide an analytical outcome representing the sample.
3. The method described in claim 2 wherein causing the microscope to analyze the sample comprises obtaining the protocol identified by interrogating the data from a database comprising one or more identifiable protocols.
4. The method described in claim 2 wherein causing the microscope to analyze the sample comprises causing the microscope to focus on the sample or on a focal plane contained within the sample.

5. The method described in claim 2 wherein causing the microscope to analyze the sample comprises obtaining an image of the sample.

6. The method described in claim 5 wherein obtaining the image comprises
   obtaining an image scan using a lens having a low magnification;
   selecting a portion of the low magnification scan for scanning an image using a lens having a high magnification;
   obtaining an image scan at the high magnification; and
   optimizing the high magnification scan.

7. A method for high throughput microscopic analysis comprising:
   providing an automated microscope comprising a slide stage, at least one objective lens, at least one slide cassette containing at least one microscope slide therein, programmable means for operating the microscope according to a protocol, and programmable means for providing an analytical outcome;
   providing a plurality of microscope slides each containing a sample and interrogatable data thereon, wherein the plurality of slides is contained in one or more of said slide cassettes, wherein the interrogatable data provide information related to a protocol for analysis of said sample;
   sequentially transporting each of said slide cassettes into a position suitable for loading a slide to said microscope stage;
      for each of said transported slide cassettes, sequentially transporting each of said plurality of slides contained in said transported slide cassette to said microscope stage;
      interrogating the data found on each of said plurality of slides;
      positioning each of said plurality of slides on the slide stage;
      causing the microscope to analyze the sample on each of said plurality of slides in accordance with the analytical protocol encoded in the interrogatable data;
      causing the microscope to provide an analytical outcome representing the sample on each of said plurality of slides.

8. The method described in claim 7 wherein causing the microscope to analyze the sample comprises obtaining the protocol identified by interrogating the data from a database comprising one or more identifiable protocols.

9. The method described in claim 7 wherein causing the microscope to analyze the sample comprises causing the microscope to focus on the sample or on a focal plane contained within the sample.

10. The method described in claim 7 wherein causing the microscope to analyze the sample comprises obtaining an image of the sample.

11. The method described in claim 10 wherein obtaining the image comprises:
   obtaining an image scan using a lens having a low magnification;
   selecting a portion of the low magnification scan for scanning an image using a lens having a high magnification;
   obtaining an image scan at the high magnification; and
   optimizing the high magnification scan, 12. A computer-readable storage medium tangibly embodying a program of instructions executable by a computer for a method of microscopic analysis using an automated microscope comprising a slide stage, at least one objective lens, image capturing means, programmable means for operating the microscope according to a protocol, and programmable means for providing an analytical outcome;
   wherein the program comprises:
      a set of instructions for interrogating data on a microscope slide wherein the interrogatable data provide information related to a protocol for analysis of a sample included on said slide;
      a set of instructions for positioning the slide on the slide stage;
      an analyzing set of instructions for causing the microscope to analyze the sample in accordance with the analytical protocol encoded in the interrogatable data; and
      a set of instructions for causing the microscope to provide an analytical outcome representing the sample.

13. The storage medium described in claim 12 further comprising a database comprising one or more identifiable programmed protocols for analyzing a sample on a microscope slide.

14. The storage medium described in claim 13 wherein the analyzing set comprises instructions for obtaining the protocol identified by interrogating the data from the database.

15. The storage medium described in claim 12 wherein the analyzing set comprises instructions for causing the microscope to focus on the sample or on a focal plane contained within the sample.

16. The storage medium described in claim 12 wherein the analyzing set comprises instructions for obtaining an image of the sample.

17. The storage medium described in claim 16 wherein the instructions for obtaining the image comprise:
   instructions for obtaining an image scan using a microscope lens having a low magnification;
   instructions for selecting a portion of the low magnification scan for scanning an image using a microscope lens having a high magnification;
   instructions for obtaining an image scan at the high magnification; and
   instructions for optimizing the high magnification scan.

18. A computer-readable storage medium tangibly embodying a program of instructions executable by a computer for a method of high throughput microscopic analysis wherein the method uses an automated microscope comprising a slide stage, at least one objective lens, at least one slide cassette containing at least one microscope slide therein, programmable means for operating the microscope according to a protocol, and programmable means for providing an analytical outcome;
   wherein the program comprises:
      a set of instructions for sequentially transporting a each of said slide cassettes into a position suitable for loading a slide to said microscope stage;
      a set of instructions for each of said transported slide cassettes, sequentially transporting each of said plurality of slides contained in said transported slide cassette to said microscope stage;
      a set of instructions for interrogating data on each of said plurality of slides wherein the interrogatable data provide information related to a protocol for analysis of a sample included on said slide;
      a set of instructions for positioning each of said plurality of slides on a slide stage;
      a set of instructions for causing the microscope to analyze the sample in accordance with the analytical protocol encoded in the interrogatable data;

a set of instructions for causing the microscope to provide an analytical outcome representing the sample on each of said plurality of slides.

19. The storage medium described in claim 18 further comprising a database comprising one or more identifiable programmed protocols for analyzing a sample on a microscope slide.

20. The storage medium described in claim 19 wherein the analyzing set comprises instructions for obtaining the protocol identified by interrogating the data from the database.

21. The storage medium described in claim 18 wherein the analyzing set comprises instructions for causing the microscope to focus on the sample or on a focal plane contained within the sample.

22. The storage medium described in claim 18 wherein the analyzing set comprises instructions for obtaining an image of the sample.

23. The storage medium described in claim 22 wherein the instructions for obtaining the image comprise:
   instructions for obtaining an image scan using a lens having a low magnification;
   instructions for selecting a portion of the low magnification scan for scanning an image using a lens having a high magnification;
   instructions for obtaining an image scan at the high magnification; and
   instructions for optimizing the high magnification scan.

24. A method comprising:
   obtaining a slide containing electronically interrogatable data recorded therewith and having a biological sample thereon;
   reading said electronically-interrogatable data from said slide;
   determining from said electronically-interrogatable data how said biological sample is to be scanned by an automated microscope;
   scanning with an automated microscope said slide in the manner dictated by the electronically-interrogatable data recorded therewith; and
   determining from said scans a test outcome, indicative of said biological sample.

* * * * *